US009132238B2

(12) United States Patent
Ferreri et al.

(10) Patent No.: US 9,132,238 B2
(45) Date of Patent: Sep. 15, 2015

(54) BLOW FILL SEAL LUER SYRINGE (71) Applicant: Becton, Dickinson and Company, Franklin Lakes, NJ (US)

(72) Inventors: Suzanne Ferreri, Ridgewood, NJ (US); Adam Zerda, Oak Ridge, NJ (US); James J. Kennedy, III, Mont Vernon, NH (US); Lee Panecki, Newton, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 45 days.

(21) Appl. No.: 13/925,185

(22) Filed: Jun. 24, 2013

(65) Prior Publication Data
US 2013/0345672 A1  Dec. 26, 2013

Related U.S. Application Data (60) Provisional application No. 61/664,424, filed on Jun. 26, 2012.

(51) Int. Cl.
| | | |
|---|---|---|
| *A61M 5/178* | (2006.01) | |
| *A61M 5/31* | (2006.01) | |
| *A61M 39/24* | (2006.01) | |
| *A61M 39/10* | (2006.01) | |
| *A61M 25/00* | (2006.01) | |
| *B65D 35/24* | (2006.01) | |

(52) U.S. Cl.
CPC .............. *A61M 5/3129* (2013.01); *A61M 25/00* (2013.01); *A61M 39/10* (2013.01); *A61M 39/24* (2013.01); *B65D 35/24* (2013.01); *A61M 2025/0019* (2013.01)

(58) Field of Classification Search
CPC ............ A61J 1/067; A61J 1/2096; A61J 1/10; A61J 2001/2027; A61J 1/1412; A61M 5/282; A61M 39/24
USPC ............. 53/452; 206/532; 604/125, 212, 247, 604/507
See application file for complete search history.

(56) References Cited

U.S. PATENT DOCUMENTS

| | | | |
|---|---|---|---|
| 4,813,941 A | 3/1989 | Shea | |
| 5,509,906 A * | 4/1996 | Poynter | 604/212 |
| 5,624,407 A * | 4/1997 | Claro | 604/216 |
| 6,173,852 B1 * | 1/2001 | Browne | 215/247 |
| 6,379,342 B1 * | 4/2002 | Levinson | 604/310 |
| 6,383,166 B1 * | 5/2002 | Farris | 604/187 |
| 6,918,418 B1 * | 7/2005 | Farris | 141/319 |
| 2002/0007155 A1 * | 1/2002 | Freund et al. | 604/232 |
| 2008/0132854 A1 * | 6/2008 | Sharp | 604/240 |

(Continued)

FOREIGN PATENT DOCUMENTS

| | | |
|---|---|---|
| WO | WO-9830188 | 7/1998 |
| WO | WO-00/06230 | 10/2000 |
| WO | WO-2010/080897 A1 | 7/2010 |

OTHER PUBLICATIONS

"PCT International Search Report for PCT/US2013/047863", Feb. 12, 2013, 5 pages.

*Primary Examiner* — Gerald Landry, II
(74) *Attorney, Agent, or Firm* — Servilla Whitney LLC (57) ABSTRACT

A single use pre-filled delivery device comprising a deformable container, a one-way valve, and male luer connector is described. Also described are methods of flushing vascular access devices using a single use pre-filled delivery device as described herein is also disclosed.

10 Claims, 13 Drawing Sheets

(56) References Cited

U.S. PATENT DOCUMENTS

| | | | |
|---|---|---|---|
| 2009/0230077 A1* | 9/2009 | Poynter et al. | 215/249 |
| 2011/0248045 A1* | 10/2011 | Harris et al. | 222/94 |
| 2012/0191067 A1* | 7/2012 | Chia et al. | 604/506 |
| 2012/0215203 A1* | 8/2012 | Alvey et al. | 604/514 |
| 2013/0199643 A1* | 8/2013 | Domkowski et al. | 137/798 |

* cited by examiner

BLOW FILL SEAL LUER SYRINGE

CROSS-REFERENCE TO RELATED APPLICATIONS

This application claims priority under 35 U.S.C. §119(e) to U.S. Provisional Application No. 61/664,424, filed Jun. 26, 2012, the disclosures of which are incorporated herein by reference in their entirety.

TECHNICAL FIELD

An aspect of the invention relates generally to vascular access device (VAD) delivery devices and particularly to VAD delivery devices comprising a manually deformable container, a male luer connector, and a one-way valve, for use in VAD flush procedures.

BACKGROUND

Vascular Access Devices (VADs) are commonly used therapeutic devices and include intravenous catheters, syringes, extension sets, stop cocks, tubing, high pressure extension tubing, and needleless access devices. The operation of VADs is often compromised or completely prevented by the occurrence of thrombus formation. Thrombosis is the development of a blood clot within a vessel and/or vascular access device. If not properly maintained, VADs can become occluded. To ensure VADs are used properly and do not become occluded, standards of practice have been developed. These standards include a cleaning procedure, which is commonly referred to as a flush procedure. The purpose of flushing is to clean the accumulated residue from dead-space located between male and female luer connections. The common flushing practice creates a turbulent flow during flushing to promote a "scrubbing" effect in the lumen and at the tip of the catheter.

VAD standards of practice usually recommend that flush procedures be performed after catheter placement, before fluid infusion, and before and after drug administration, blood sampling, transfusions and parenteral nutrition. The goal of these flush procedures is to confirm catheter patency, avoid drug incompatibilities, ensure complete drug dose administration, prevent thrombus formation and minimize the risk of blood stream infections. Flush procedures require different types and amounts of flush solutions. The most commonly used flush solutions are saline and/or heparin lock solution. The type of flush solution and amount vary depending on the specific type of catheter. Flush solution volumes between 5 and 10 ml are most common but can range from 1 ml to 20 ml.

One form of VAD maintenance typically used includes a continuous saline drip where a saline bag is connected to the VAD and provides continuous flow of saline solution to the patient through the VAD. This approach may put the patient at risk by delivering excess fluid to the vascular space. An alternative method for vascular device maintenance, known as flushing, involves intermittent delivery of saline through the VAD using a hypodermic syringe.

The effectiveness of the flushing procedure in intravenous therapy is related to the risk of microbial colonization and potential Catheter Related Bloodstream Infection (CRBSI). Thus, the greater the amount of blood and residue remaining in the catheter system, the higher the risk for infection and complications related to infection.

SUMMARY

Embodiments of the present invention are directed to a single use device for VAD flush applications. One aspect of the invention is directed to a VAD delivery device having a manually deformable liquid container, a male luer connector, and a one-way valve. The container defines an inner chamber and has a distal end, a proximal end, and an outlet on the distal end. The male luer connector projects from the outlet on the distal end of the container and is in fluid communication with the inner chamber of the container. The male luer connector is engagable with a luer connector of a VAD. The one-way valve is engaged with the male luer connector and is in fluid communication with the inner chamber of the container. The one-way valve is configured to prevent fluid flow in the direction outside the inner chamber to inside the inner chamber when the container is manually deformed and released.

In one or more embodiments, the VAD delivery device may also include a molded cap releasably connected to the container. The molded cap may be configured to encase the male luer connector and seal the inner chamber of the container.

The one-way valve may be a duckbill valve, an umbrella valve, or a combination umbrella, duckbill valve.

In one or more embodiments, the inner chamber of the container may have a volume in the range of about 0.5 mL to 10 mL.

The container may be made of any suitable thermoplastic elastomer and may be pre-filled with a solution.

In one or more embodiments, the container and molded cap may be adapted to create a sterile or aseptic barrier.

A second aspect of the invention pertains to a method of flushing a VAD. The method according to one embodiment comprises providing a VAD delivery device having a manually deformable liquid container, a male luer connector, and a one-way valve, and providing a VAD having a proximal end, a distal end, and a passageway therethrough, the proximal end having a female luer tip in fluid communication with the passageway. The distal end of the VAD is placed in a blood vessel of a patient and the male luer connector of the container is engaged with the female luer of the VAD. Force is applied to deform the container so that a flush solution located in the chamber flows through the one-way valve into the VAD. The male luer is then disengaged from the female luer of the VAD. As noted above, the container defines an inner chamber and has a distal end, a proximal end, and an outlet on the distal end. The male luer connector projects from the outlet on the distal end of the container and is in fluid communication with the inner chamber of the container. The male luer connector is engagable with a luer connector of a VAD. The one-way valve is engaged with the male luer connector and is in fluid communication with the inner chamber of the container. The one-way valve is configured to prevent fluid flow in the direction outside the inner chamber to inside the inner chamber when the container is manually deformed and released.

Although a wide variety of catheters and I.V. ports can be adequately flushed using currently available syringe assemblies, as flushing practices change from continuous IV drip to intermittent flushing, there is a need for a new sterile, single use, pre-filled delivery device for maintenance of VAD's.

DETAILED DESCRIPTION

Before describing several exemplary embodiments of the invention, it is to be understood that the invention is not limited to the details of construction or process steps set forth in the following description. The invention is capable of other embodiments and of being practiced or being carried out in various ways.

In this disclosure, a convention is followed wherein the distal end of the device is the end closest to a patient and the proximal end of the device is the end away from the patient and closest to a practitioner.

As used herein, the term "luer connector" refers to a connection collar that is the standard way of attaching syringes, catheters, hubbed needles, IV tubes, etc. to each other. The Luer connector consists of male and female interlocking tubes, slightly tapered to hold together better with even just a simple pressure/twist fit. Luer connectors can optionally include an additional outer rim of threading, allowing them to be more secure. The Luer connector male end is generally associated with a flush syringe and can interlock and connect to the female end located on the VAD. A Luer connector comprises a distal end, a proximal end, an irregularly shaped outer wall, a profiled center passageway for fluid communication from the chamber of the barrel of a syringe to the hub of a VAD. A Luer connector also has a distal end channel that releasably attaches the Luer connector to the hub of a VAD, and a proximal end channel that releasably attaches the Luer connector to the barrel of a syringe.

The term "deformable" refers to a wall or container that is structured to be flexible enough to collapse at least partially into the inner chamber under manual depression. The shape and extent of the deformation will vary with the various configurations of the inner chamber and deformable container.

The present invention overcomes problems associated with known flushing techniques and flush devices by providing a single use disposable VAD delivery apparatus that effectively scrubs the blood residue and other debris from deadspace located between the male/female luer connections, as well as other parts of the VAD. A single use sterile delivery device overcomes problems found with the prior art by reducing the risk associated with contamination due to manually filling a syringe with solution from a vial. Other advantages of this invention over prior art include the following: a) the delivery device of the present invention is capable of generating a secure connections with a receiving needleless female vascular access connector and delivers a solution; b) the incorporation of a one-way valve, as disclosed in the present invention, enables delivery of solution using a deformable and collapsible container with minimal reflux; and c) the VAD delivery device of the present invention can be made using the blow, fill, seal process, which enables the creation of a sterile and protected luer connector.

Figure 1:
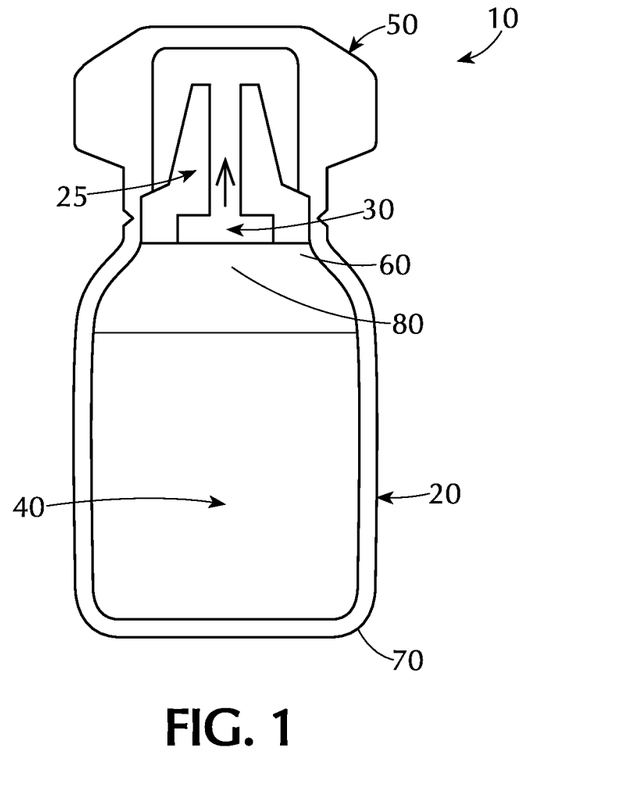
FIG. 1 shows a perspective view of an exemplary VAD delivery device having a deformable container, a male luer, one-way valve, and molded cap.
Figure 2:
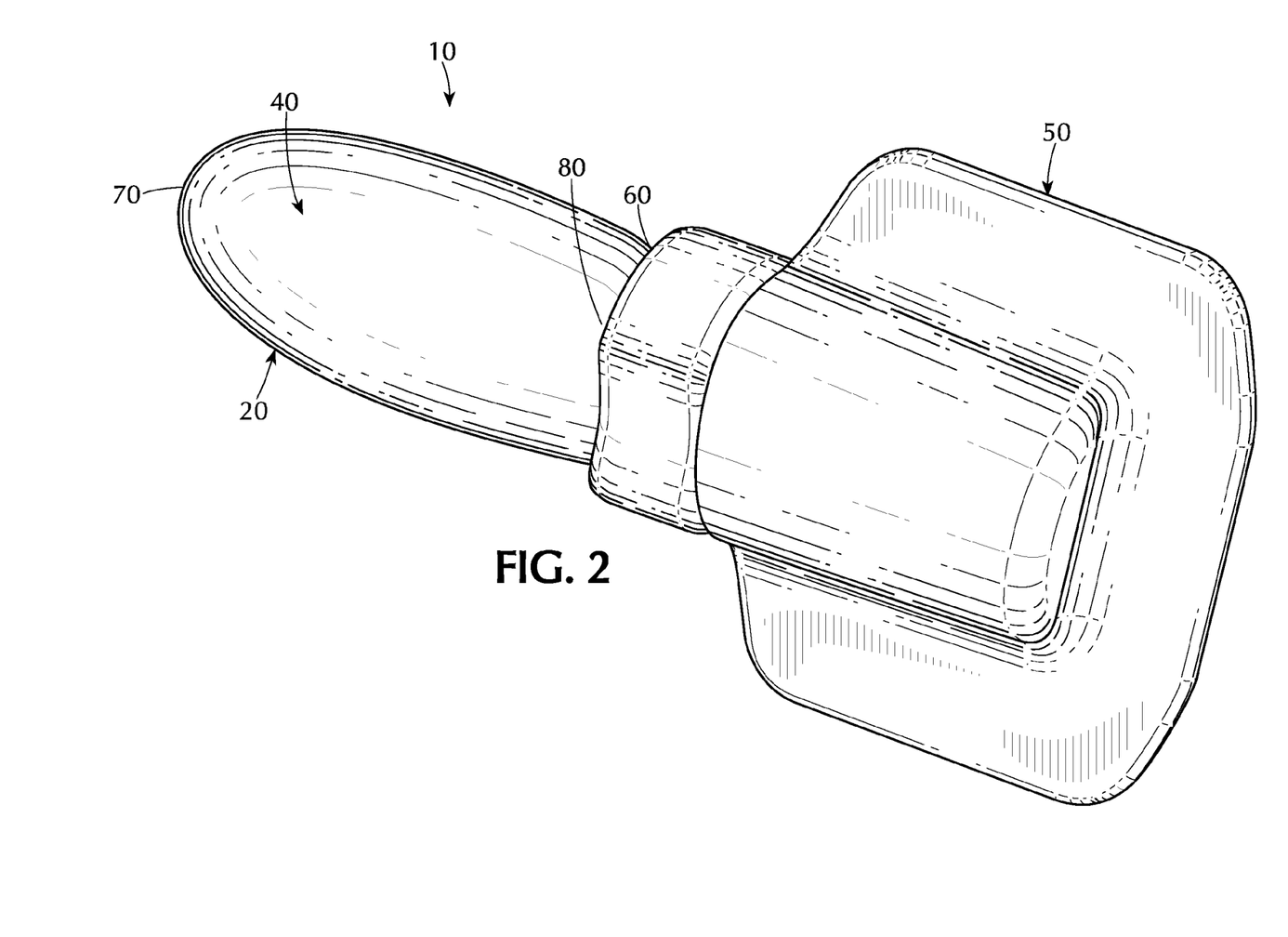
FIG. 2 shows a perspective view of an exemplary VAD delivery device having a molded cap and deformable container.
Figure 3:
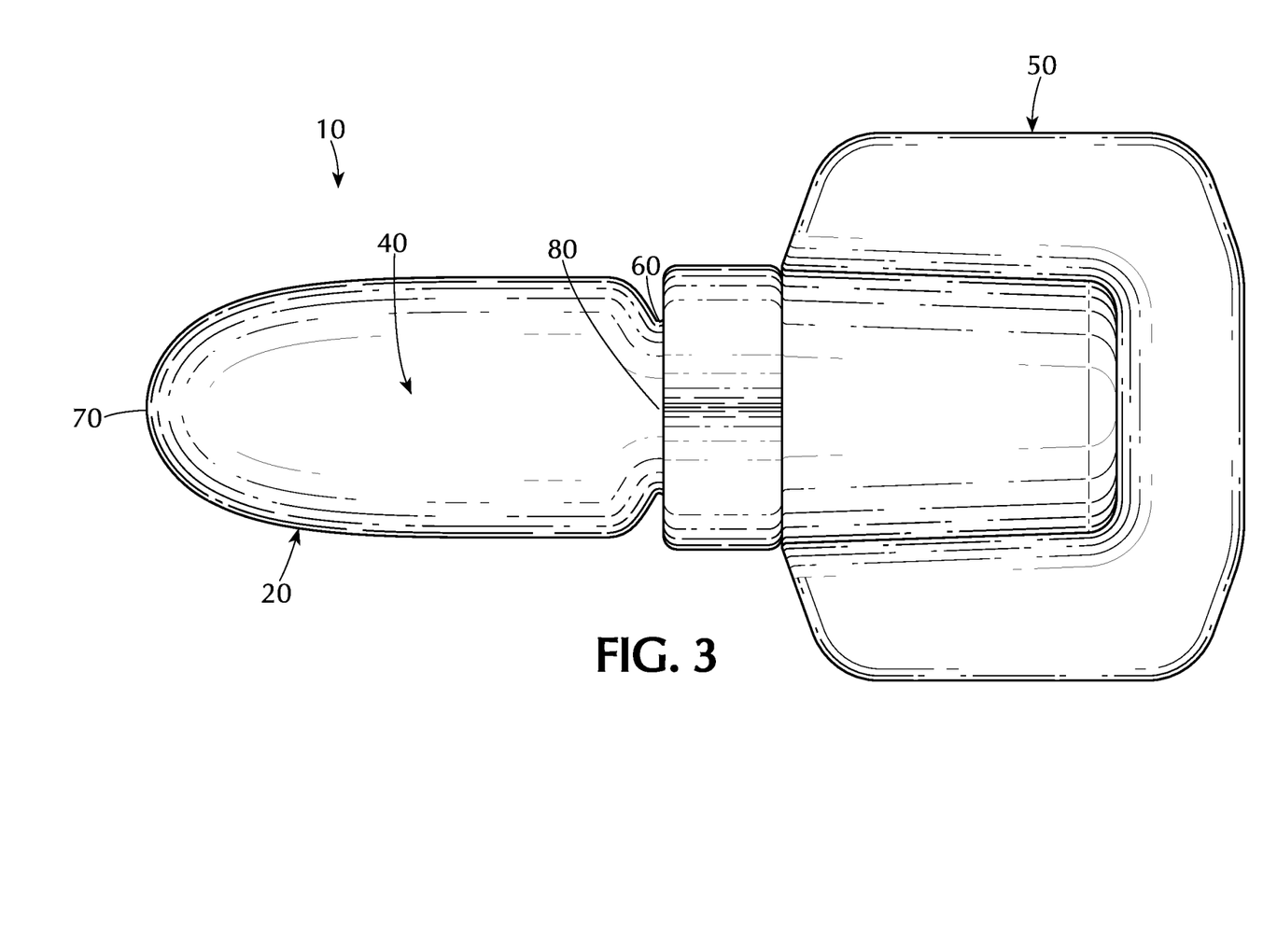
FIG. 3 shows a top view of the VAD delivery device showing a molded cap and deformable container.
Figure 4:
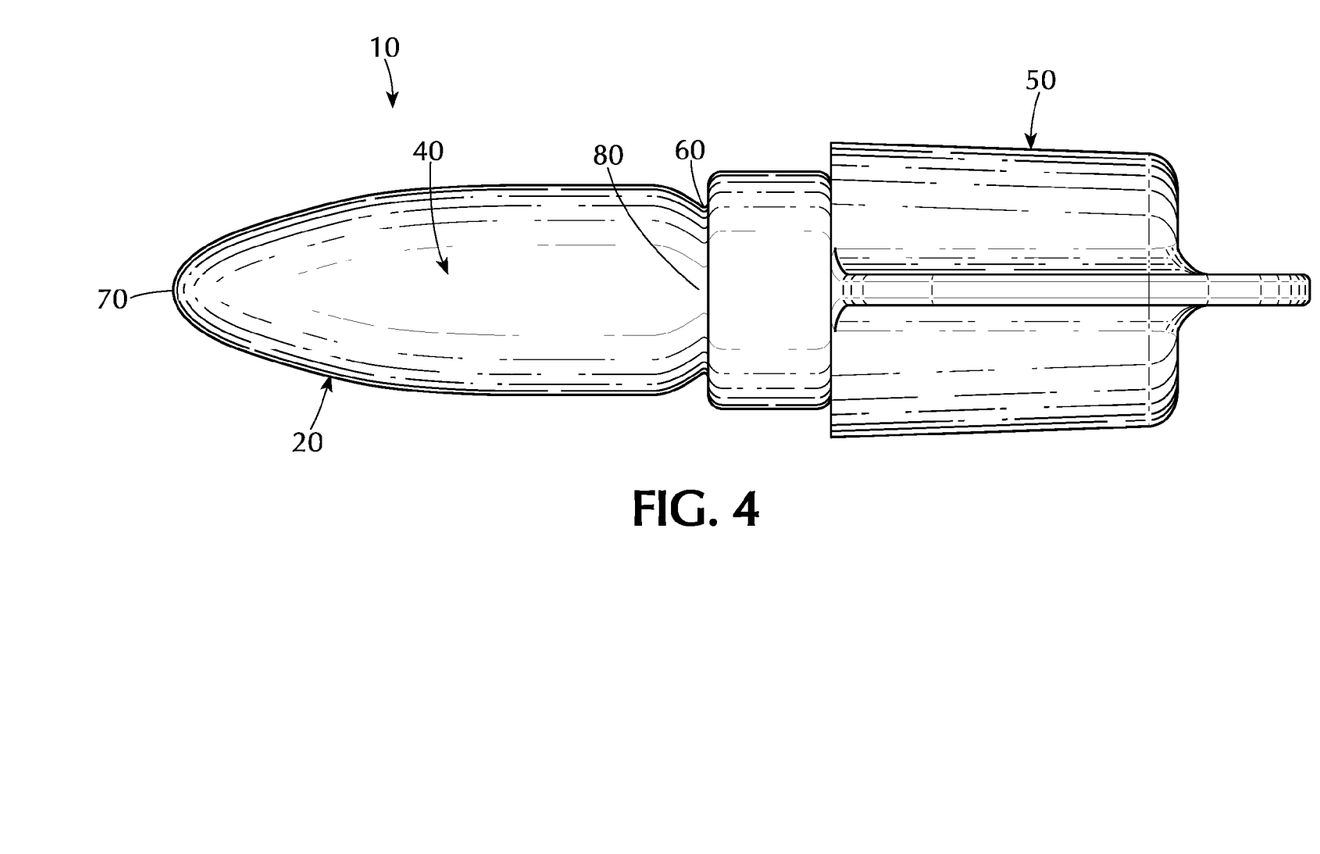
FIG. 4 shows a right side view of an exemplary VAD delivery device showing a molded cap and deformable container.
Figure 5:
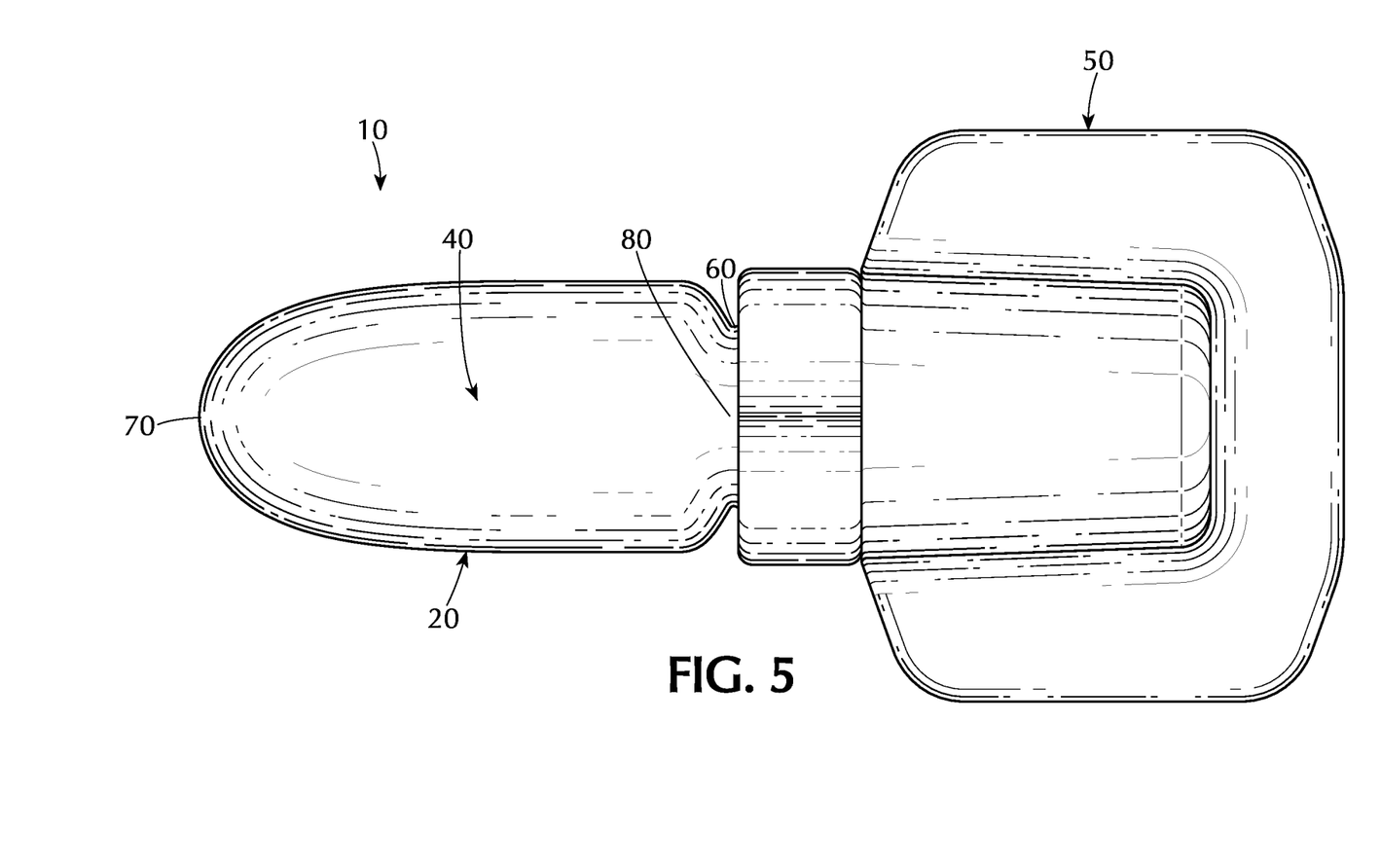
FIG. 5 shows a top view of an exemplary VAD delivery device having a molded cap and deformable container.
Figure 6:
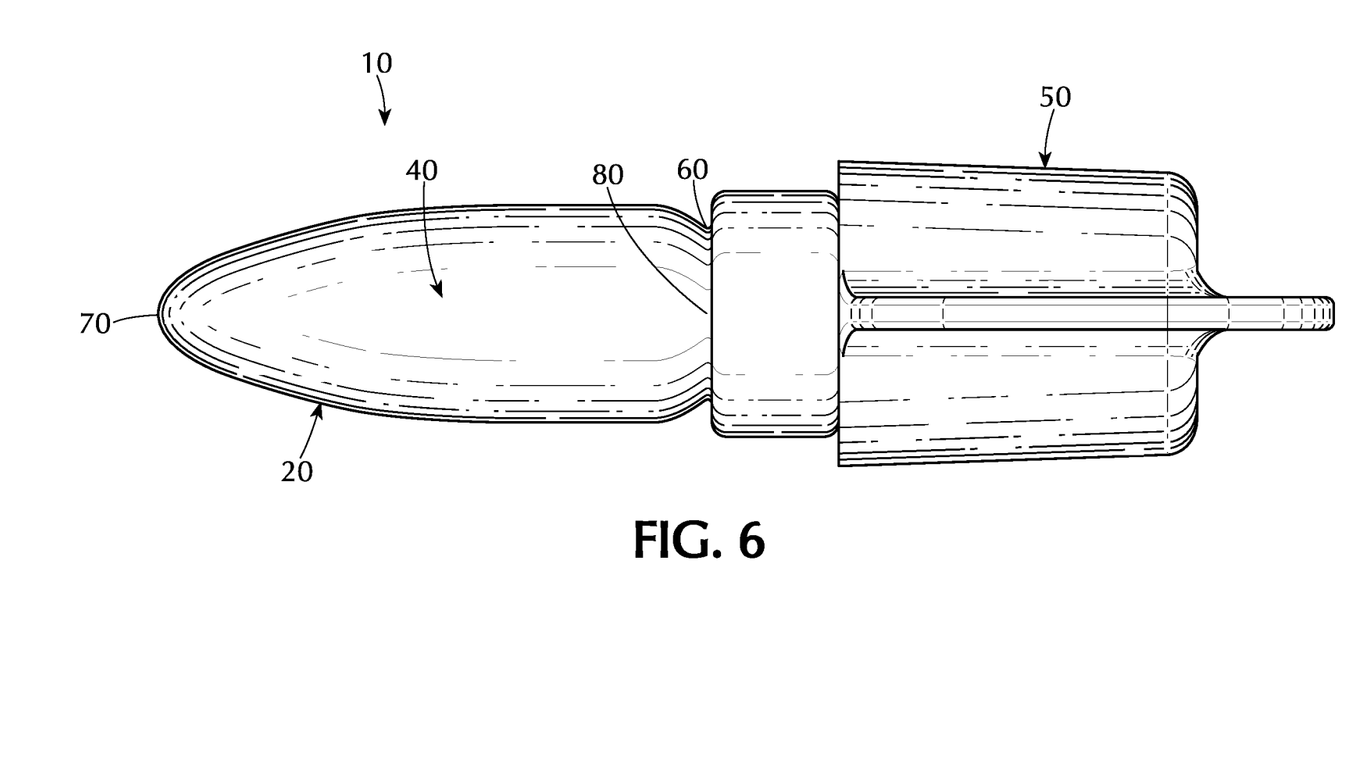
FIG. 6 shows a side view of an exemplary VAD delivery device having a molded cap and deformable container.
Figure 7A:
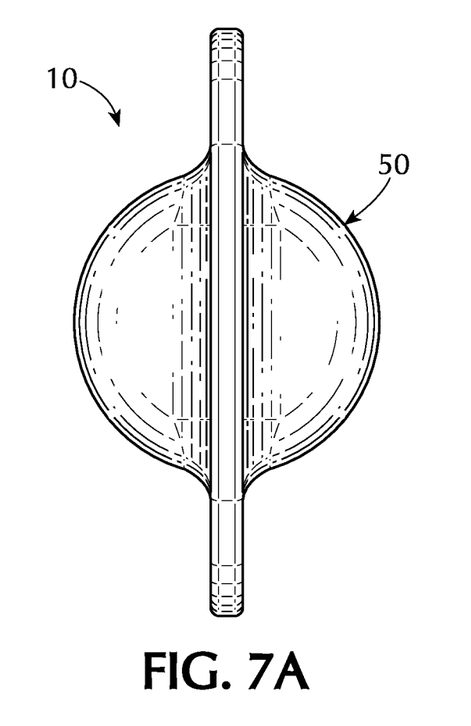
FIG. 7A shows a front view of an exemplary VAD delivery device, viewed directly from the distal end, showing a molded cap.
Figure 7B:
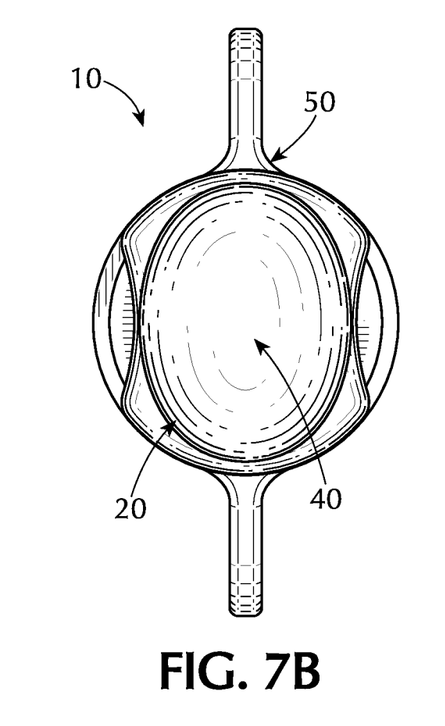
FIG. 7B shows a back view of an exemplary VAD delivery device, viewed directly from the proximal end, showing a deformable container and a molded cap.
Figure 8:
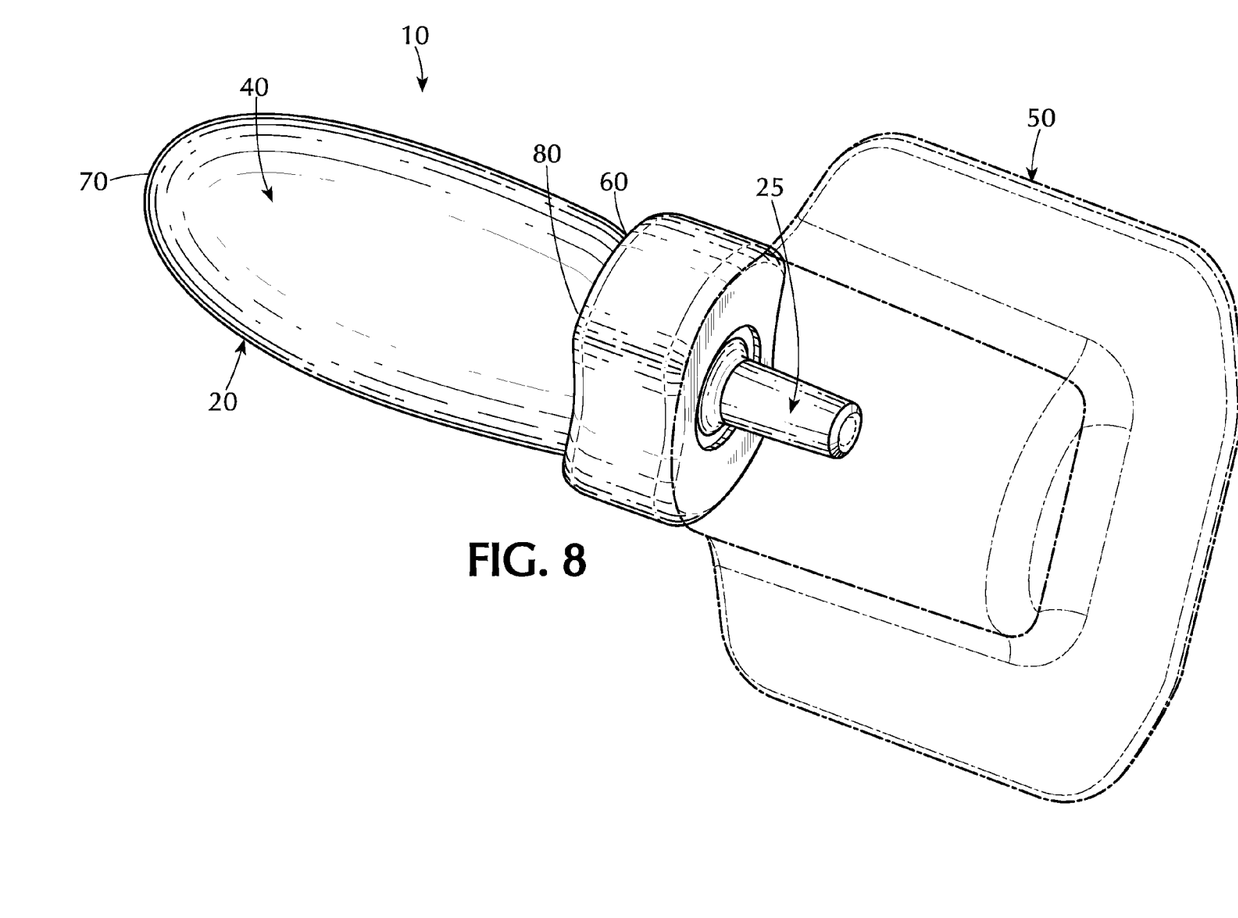
FIG. 8 shows a perspective view of an exemplary VAD delivery device having a molded cap, a deformable container and male luer connector.
Figure 9:
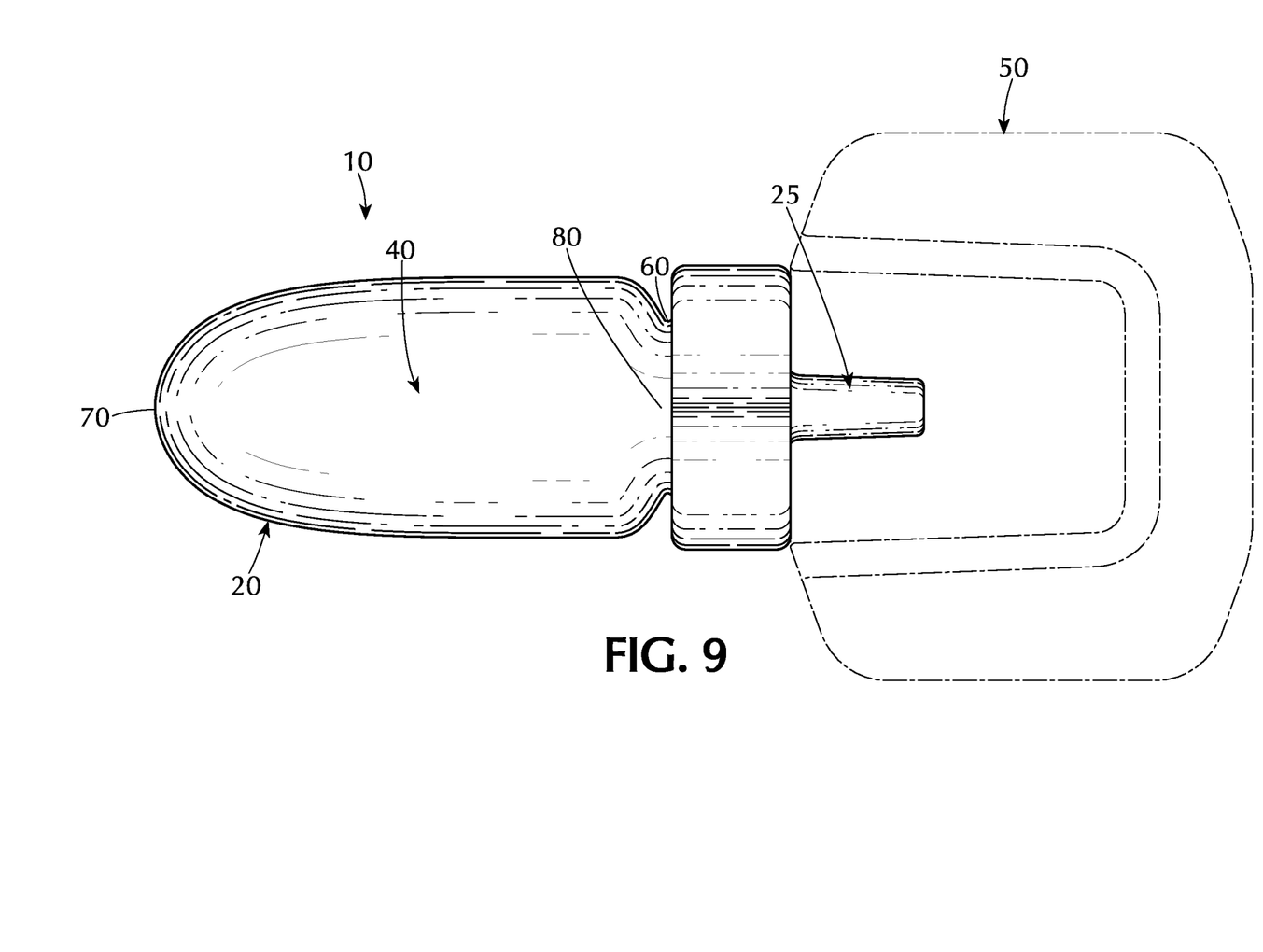
FIG. 9 shows a top view of an exemplary VAD delivery device having a molded cap, a deformable container and male luer connector.
Figure 10:
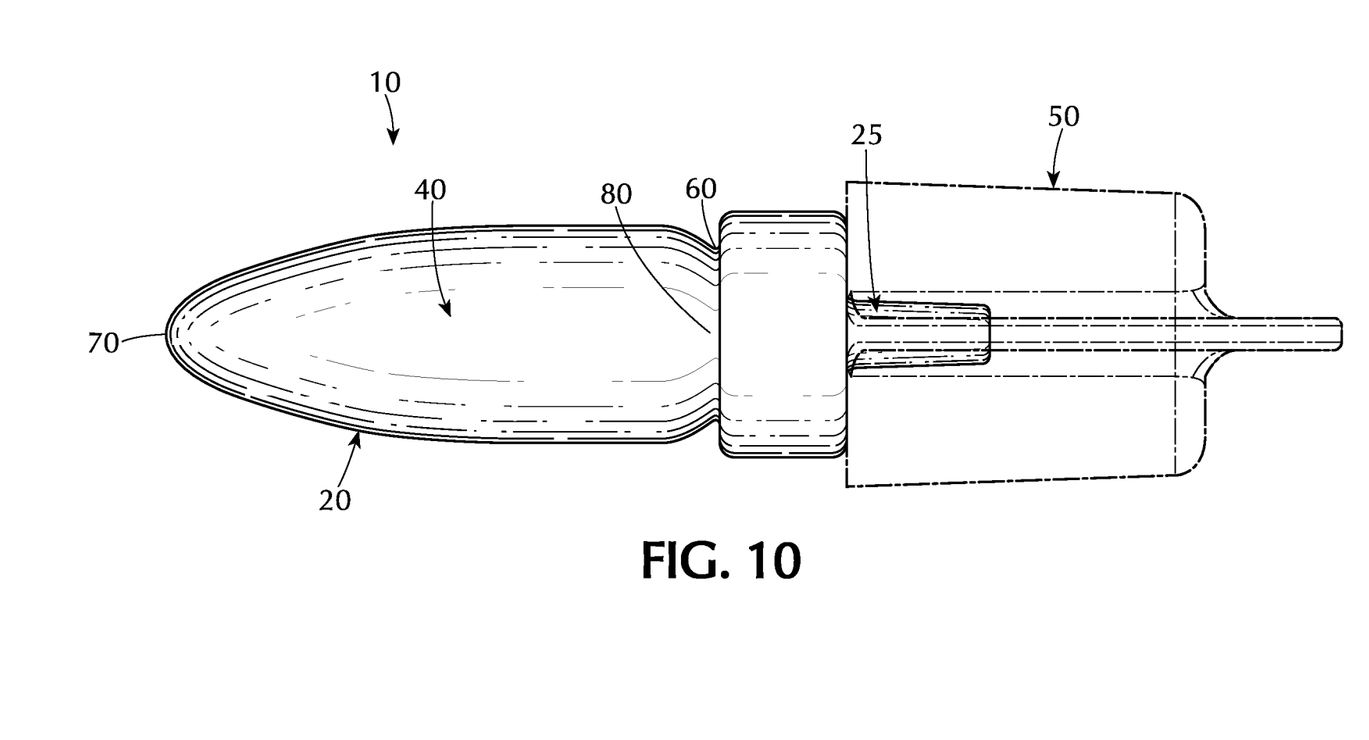
FIG. 10 shows a right side view of an exemplary VAD delivery device having a molded cap, a deformable container and male luer connector.
Figure 11:
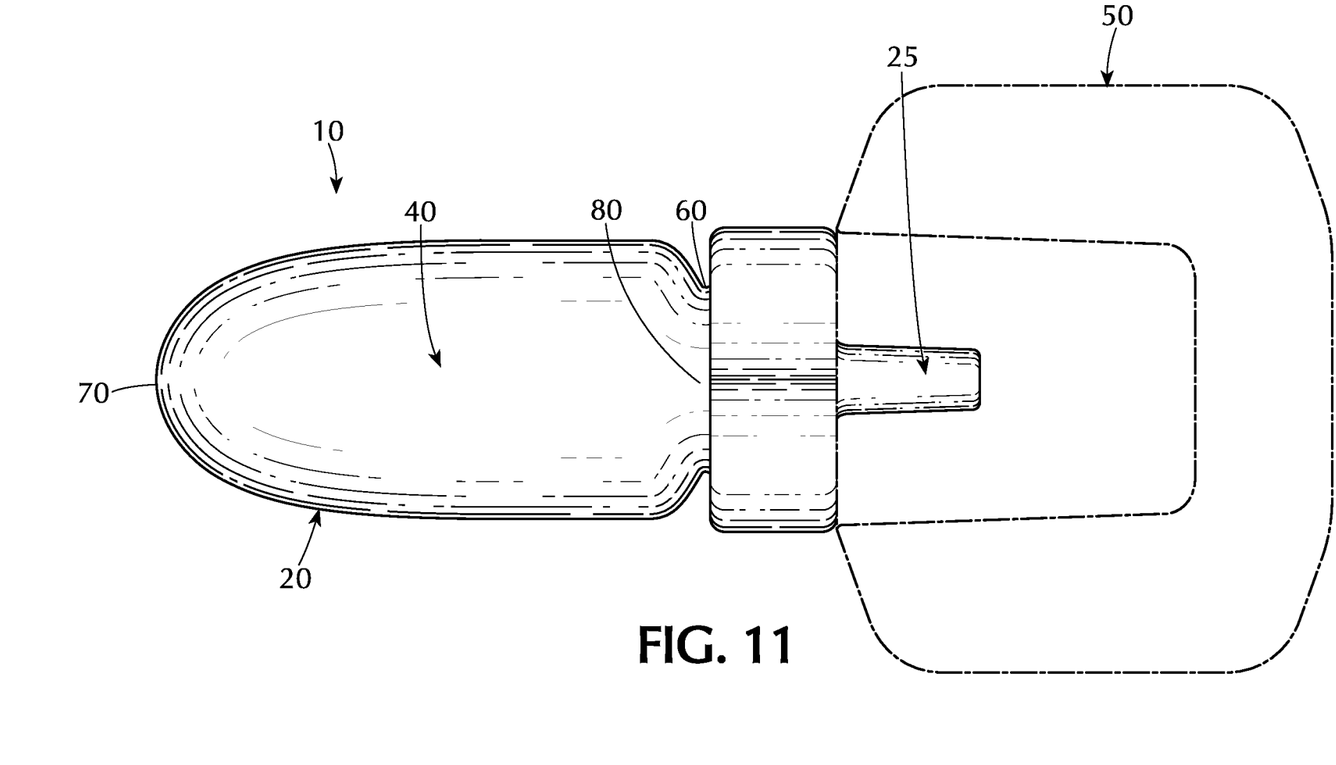
FIG. 11 shows a top view of an exemplary VAD delivery device having a molded cap, a deformable container and male luer connector.
Figure 12:
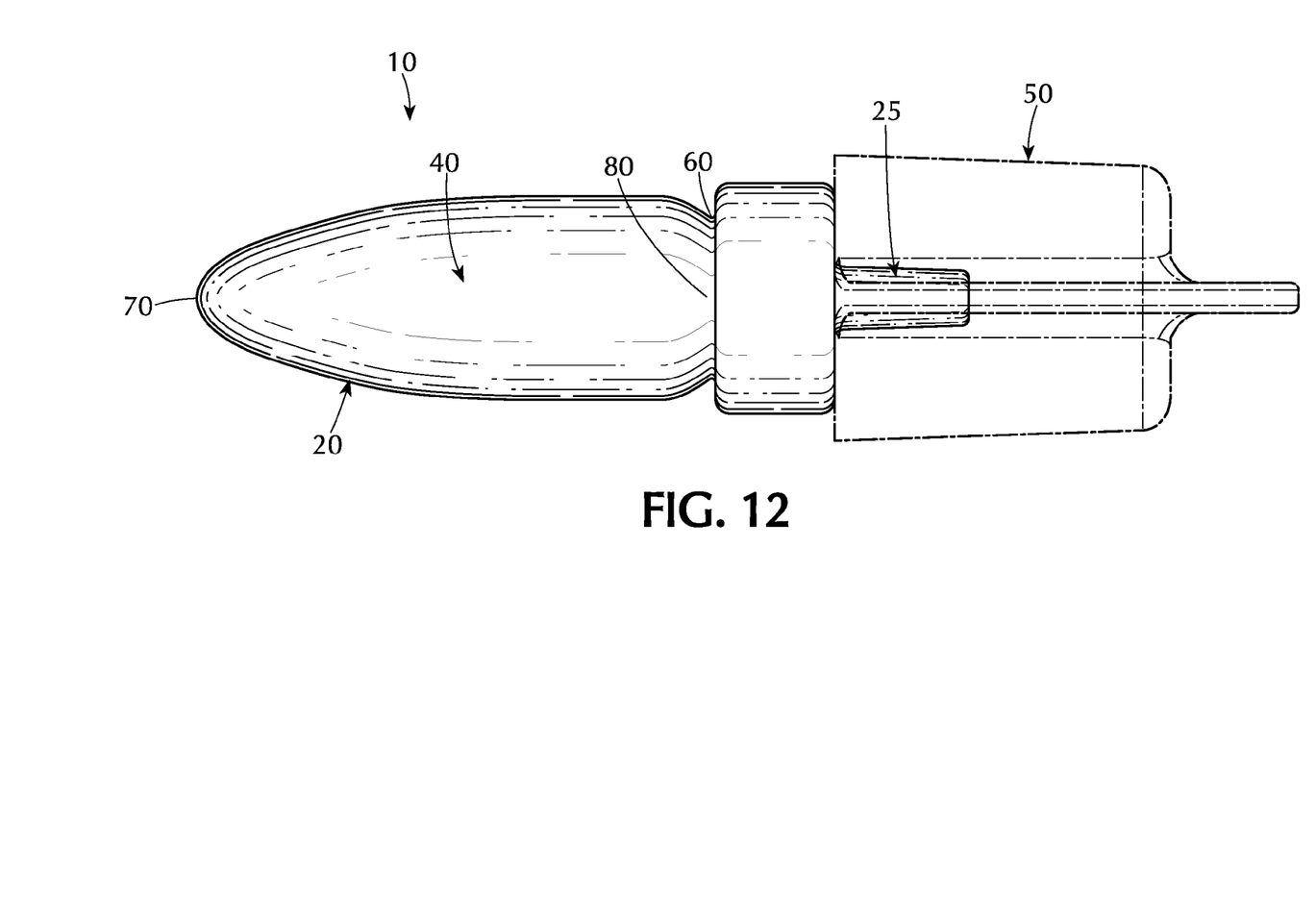
FIG. 12 shows a side view of an exemplary VAD delivery device having a molded cap, a deformable container and male luer connector.
Figure 13:
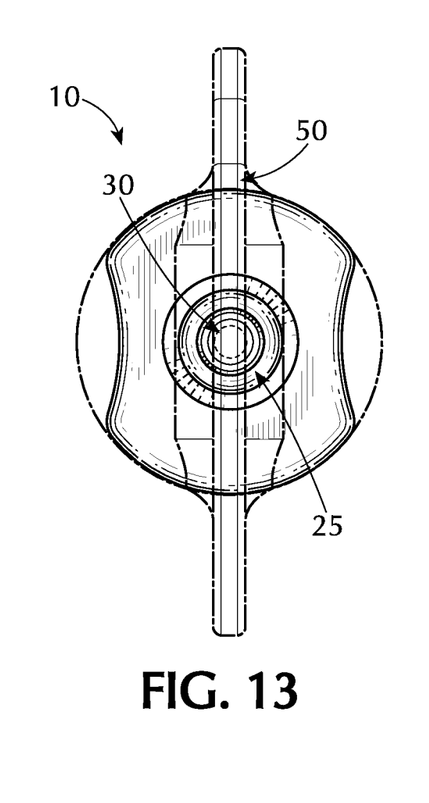
FIG. 13 shows a front view of an exemplary VAD delivery device showing a molded cap, a male luer connector and one-way valve are also shown.
Figure 14:
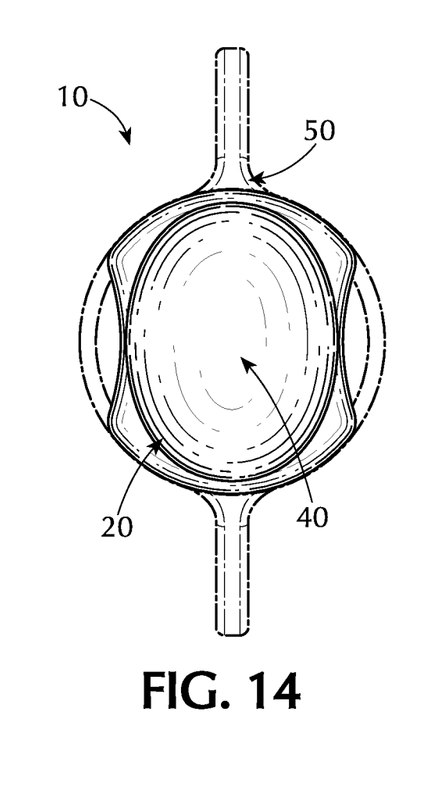
FIG. 14 shows a back view of an exemplary VAD delivery device showing a deformable container and a molded cap.

FIGS. 1-14 illustrate an exemplary VAD delivery device 10 according to the present invention. In one or more embodiments, the VAD delivery device 10 generally comprises a manually deformable liquid container 20, a male luer connector 25, and a one-way valve 30. The container 20 defines an inner chamber 40 and has a distal end 60, a proximal end 70, and an outlet 80 on the distal end 60. The male luer connector 25 projects from the outlet 80 on the distal end 60 of the container 20 and is in fluid communication with the inner chamber 40 of the container 20. The male luer connector 25 is engagable with a luer connector of a VAD. The one-way valve 30 is engaged with the male luer connector 25 and is in fluid communication with the inner chamber 40 of the container 20. The one-way valve 30 is configured to prevent fluid flow in the direction outside the inner chamber 40 to inside the inner chamber 40 when the container 20 is manually deformed and released. These features allow the clinician to manually deliver a sterile solution to the female luer of a VAD using a disposable apparatus.

Blow, fill, seal technology is well known in the art and consists of generating containers that are formed, filled with liquid, and sealed in a continuous process under sterile or aseptic conditions. In one or more embodiments of the present invention, the VAD delivery device 10 may be produced using a blow, fill seal, process, in which the delivery device is created in a single manufacturing step. The single use pre-filled delivery device 10 of the present invention may be manufactured in accordance with a blow-fill-seal technique of a character well understood by those skilled in the art. The concept of a blow-fill-seal process is that a container is formed, filled, and sealed as a unitary container in a continuous manner without human intervention in a sterile, enclosed area inside a machine. Blow-fill-seal manufacturing forms a closed container by extruding and forming a parison within a mold, filling the container and sealing the container in a single step. This manufacturing process enables the device to be produced in a single process. For example, pharmaceutical grade resin is extruded into a tube, which is then formed into a container. A mandrel is inserted into the newly formed container and filled. The container is then sealed, all inside a sterile, shrouded chamber. The product is then discharged to a non-sterile area for packaging and distribution. This blow-fill-seal technique comprises the continuous extrusion through an extruder head of a length of a parison in the form of a hollow tube between and through two co-acting first or main mold halves. The method includes the step of cutting off the parison below the extruder head and above the main mold halves to create an opening which allows a blowing and filling nozzle assembly to be moved downwardly into the opening in the parison for molding and thereafter filling a molded container. When the container portion of the container assembly is filled with the desired amount of liquid, the blowing and filling nozzle assembly is retracted from the opening in the parison. A separate pair of co-acting second or upper sealing mold halves are then moved together around the exposed length of parison to form and seal the container upper portion. The finished container assembly, completely formed, filled, and sealed as a unitary structure is then conveyed out of the molding apparatus.

In one or more embodiments, the luer connector 25 is a molded part that is inserted into the container 20 during the blow, fill, seal process. The one-way valve 30 is a separately molded part that is inserted within the fluid path of the luer connector 25 to limit flow of solution to a single direction from within the container 20 to the vascular access connector. In another embodiment, the luer connector 25 is molded directly to the container 20 using the blow, fill, seal process. In this configuration, the one-way valve 30 is sealed within the luer path using the blow, fill, seal process.

In one or more embodiments, the one-way valve 30 is a separately molded part that is continuous with the fluid path of the luer connector 25 and is in fluid communication with the inner chamber 40 of the deformable container 20. The one-way valve 30 may be configured to enable delivery of solution from a deformable container 20 with minimal reflux. It is contemplated that any mechanism suitable for preventing the flow of solution from outside to inside the container may be used. In one or more embodiments, the one-way valve 30 may comprise a duckbill, umbrella valve, combination duckbill-umbrella valve, ball-check valve, diaphragm-check valve, swing-check valve, tilting disk-check valve, stop-check valve, lift-check valve or any combination of one-way valves. In one or more embodiments, the one-way valve 30 is configured to allow for fluid flow in one direction when the pressure inside the container 20 is above a threshold level and configured to prevent fluid flow when the pressure inside the container 20 drops below the threshold level. The one-way valve 30 may be configured to allow flow under pressure levels consistent with manually deforming the container 20 by hand. The delivery device 10 with the deformable container 20 and valve 30, allows for flow under typical hand forces and stops flow when the pressure inside the deformable container 20 falls below that within the luer area of the device.

In one or more embodiments, the VAD delivery device 10 may also include a molded cap 50 releasably connected to the container 20, configured to encase the male luer connector 25 and seal the inner chamber of the container. The molded cap 50 can be manually released from the rest of the VAD delivery device by hand. In one or more embodiments, the molded cap 50 can extend outward from the distal end 60 of the container 20, configured to be readily gripped by hand for removal. The molded cap 50 may be configured for release under forces consistent with manual removal by hand.

In one or more embodiments, the VAD delivery device 10 may include a male luer connector 25 configured to engage with a female luer connector of a VAD. Male and female luer connectors are well known in the art and consist of standard fittings designed to make leak-free connections between male and female luers for transfer of fluid. In one or more embodiments, the VAD delivery device 10 may include a male luer connector 25 of a luer-lok or luer-slip design. The luer-lok and luer-slip varieties of luer connectors are well known in the art.

In one or more embodiments, the luer connector 25 may be configured to maintain a leak free connection under pressure levels required for fluid flow from the container, through the one-way valve, to the VAD.

The dimensions of the luer connection of the present invention can be made to comply with applicable standards and/or regulations, such as ISO standard 594.

In one or more embodiments, the VAD delivery device 10 may include a container 20 configured for manual deformation. The container may define an inner chamber 40 having a volume in the range of about 0.5 mL to 10 mL. However, VAD delivery device 10 would readily function with a container 20 holding a volume below 0.5 and above 10 mL. In one or more embodiments, the container 20 may be generated during the blow, fill, seal process to achieve a suitable size and shape. In one or more embodiments, the container 20 takes on a generally round or oval shape, however, the present invention would function if the container 20 was configured to any shape that is readily deformable.

The delivery device 10 of the present invention may be used in conjunction with a vascular access device having a proximal end, a distal end and a passageway therethrough, said proximal end of the VAD having a female luer tip in fluid communication with said passageway. To use the delivery device 10 in a flushing procedure, the user engages the male luer connector 25 of the deformable container 20 of the delivery device 10 with the female luer tip of a vascular access device after the distal end of said vascular access device has been placed in a blood vessel of a patient. The user then applies force to deform the container 20 so that a flush solution located in the inner chamber 40 flows through the one-way valve 30 into the VAD. The male luer connector 25 is then disengaged from the female luer of the VAD.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A vascular access device (VAD) delivery device comprising:
 a manually deformable liquid container defining an inner chamber, the container having a distal end, a proximal end, and an outlet on the distal end;
 a male luer connector projecting from the outlet on the distal end of the container, the male luer connector in fluid communication with the inner chamber of the container and engageable with a luer connector of a VAD; and a one-way valve engaged with the male luer connector, the one-way valve in fluid communication with the inner chamber of the container, the one-way valve preventing fluid flow in the direction outside the inner chamber to inside the inner chamber when the container is manually deformed and released.

2. The VAD delivery device as claimed in claim 1, further comprising a molded cap releasably connected to the container, the molded cap configured to encase the male luer connector and seal the inner chamber of the container.

3. The VAD delivery device as claimed in claim 1, wherein the one-way valve comprises a duckbill valve, umbrella valve, combination duckbill-umbrella valve, ball-check valve, diaphragm-check valve, swing-check valve, tilting-disk check valve, stop-check valve, poppet-check valve, or lift-check valve.

4. The VAD delivery device as claimed in claim 1, wherein the inner chamber of the container has a volume in the range of about 0.5 mL to 10 mL.

5. The VAD delivery device as claimed in claim 1, wherein the container comprises a thermoplastic elastomer.

6. The VAD delivery device as claimed in claim 2, wherein the container and molded cap are adapted to create an aseptic or sterile barrier.

7. The VAD delivery device as claimed in claim 1, wherein the container is pre-filled with solution.

8. The VAD delivery device as claimed in claim 1, wherein the male luer connector is molded directly using the blow, fill, seal process.

9. The VAD delivery device as claimed in claim 1, wherein the male luer connector is a separately molded part that is inserted into the distal outlet during the blow, fill, seal process.

10. A method of flushing a VAD comprising:

providing a vascular access delivery device having a manually deformable liquid container defining an inner chamber, the container having a distal end, a proximal end, and an outlet on the distal end, a male luer connector projecting from the outlet on the distal end of the container, the male luer connector in fluid communication with the inner chamber of the container and engageable with a luer connector of a VAD, and a one-way valve engaged with the male luer connector, the one-way valve in fluid communication with the inner chamber of the container, the one-way valve preventing fluid flow in the direction outside the inner chamber to inside the inner chamber when the container is manually deformed and released;

providing a VAD having a proximal end, a distal end, and a passageway therethrough, the proximal end having a female luer tip in fluid communication with the passageway;

placing the distal end of the VAD in a blood vessel of a patient;

engaging the male luer connector of the container with the female luer of the VAD;

applying force to deform the container so that a flush solution located in the chamber flows through the one-way valve into the VAD; and disengaging the male luer connector of the container from the female luer of the VAD.

\* \* \* \* \*